(12) United States Patent
Smith et al.

(10) Patent No.: US 7,524,984 B2
(45) Date of Patent: *Apr. 28, 2009

(54) PHASE CHANGE SOLVENTS

(75) Inventors: Steven Daryl Smith, Fairfield, OH (US); Mark William Hamersky, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 381 days.

This patent is subject to a terminal disclaimer.

(21) Appl. No.: 10/429,531

(22) Filed: May 5, 2003

(65) Prior Publication Data
US 2004/0021130 A1 Feb. 5, 2004

Related U.S. Application Data

(60) Provisional application No. 60/399,963, filed on Jul. 31, 2002.

(51) Int. Cl.
C07C 69/76 (2006.01)

(52) U.S. Cl. ..................... 560/76; 528/308.7

(58) Field of Classification Search ............... 524/294, 524/296, 297; 560/76; 528/308.7
See application file for complete search history.

(56) References Cited

U.S. PATENT DOCUMENTS

| | | | | |
|---|---|---|---|---|
| 2,075,107 A * | 3/1937 | Frazier | .......... | 560/89 |
| 2,453,264 A | 11/1948 | Rehberg | | |
| 2,777,871 A | 1/1957 | Strain | | |
| 3,376,275 A | 4/1968 | Bayerlein et al. | | |
| 3,562,356 A | 2/1971 | Nyberg et al. | | |
| 3,734,891 A * | 5/1973 | Knopka | .......... | 528/275 |
| 3,755,231 A | 8/1973 | Muir et al. | | |
| 3,981,838 A * | 9/1976 | Wilson | .......... | 524/295 |
| 4,098,751 A | 7/1978 | Mark et al. | | |
| 4,123,413 A | 10/1978 | Mark et al. | | |
| 4,131,581 A | 12/1978 | Coker | | |
| 4,146,522 A | 3/1979 | Heckles | | |
| 4,210,568 A | 7/1980 | Makowski et al. | | |
| 4,293,473 A | 10/1981 | Eastman | | |
| 4,387,214 A | 6/1983 | Passmore et al. | | |
| 4,442,270 A | 4/1984 | Passmore et al. | | |
| 4,500,662 A | 2/1985 | Lai | | |
| 4,578,302 A | 3/1986 | Schmidt, Jr. et al. | | |
| 4,618,630 A * | 10/1986 | Knobel et al. | .......... | 521/105 |
| 4,704,110 A | 11/1987 | Raykovitz et al. | | |
| 4,738,807 A | 4/1988 | Aitken et al. | | |
| 4,745,026 A | 5/1988 | Tsukahara et al. | | |
| 4,882,375 A | 11/1989 | Tyrell et al. | | |
| 5,086,104 A | 2/1992 | Wada | | |
| 5,352,531 A | 10/1994 | Roberts et al. | | |
| 5,389,711 A | 2/1995 | Westbrook et al. | | |
| 5,418,281 A | 5/1995 | Yung et al. | | |
| 5,503,919 A | 4/1996 | Litchholt et al. | | |
| 5,534,303 A | 7/1996 | Roberts et al. | | |
| 5,534,583 A | 7/1996 | Roberts et al. | | |
| 5,540,983 A | 7/1996 | Maris et al. | | |
| 5,580,916 A | 12/1996 | Traverso et al. | | |
| 5,624,986 A | 4/1997 | Bunnelle et al. | | |
| 5,627,229 A | 5/1997 | Bunnelle et al. | | |
| 5,633,319 A | 5/1997 | Silvi et al. | | |
| 5,714,254 A | 2/1998 | Jacob | | |
| 5,853,874 A | 12/1998 | Jacob | | |
| 5,895,718 A | 4/1999 | Ishimura et al. | | |
| 5,910,527 A | 6/1999 | Alper et al. | | |
| 5,939,483 A | 8/1999 | Kueppers | | |
| 5,945,485 A | 8/1999 | Struglinski et al. | | |
| 6,080,480 A | 6/2000 | Shiba et al. | | |
| 6,117,176 A | 9/2000 | Chen | | |
| 6,177,508 B1 | 1/2001 | Ohmori et al. | | |
| 6,187,425 B1 | 2/2001 | Bell et al. | | |
| 6,703,115 B2 * | 3/2004 | Hale et al. | .......... | 428/212 |
| 6,723,444 B2 * | 4/2004 | Kobayashi et al. | .......... | 428/480 |

FOREIGN PATENT DOCUMENTS

| | | |
|---|---|---|
| EP | 0 044 675 B1 | 5/1984 |
| EP | 0 277 750 | 8/1988 |
| EP | 989162 A1 | 3/2000 |
| EP | 1 193 284 A1 | 4/2002 |
| FR | 2 488 266 A1 | 2/1982 |
| GB | 1181807 | 2/1970 |
| GB | 1190417 | 5/1970 |
| GB | 1193626 | 6/1970 |
| GB | 1193627 | 6/1970 |

(Continued)

OTHER PUBLICATIONS

Chem. Abstracts 1996:310113, "End-grafting oligoesters based on terephthalic acid and linear diols for high solids coatings" Teng et al. Journal of Applied Polymer Science (1995) 60(10), 1609-1618.*

(Continued)

Primary Examiner—Peter D Mulcahy
(74) Attorney, Agent, or Firm—Angela Marie Stone; Julie A. McConihay; John M. Howell

(57) ABSTRACT

Phase change solvents for thermoplastic polymers to provide blended compositions. Above the phase change temperature of the solvent, the phase change solvent solubilizes or intimately mixes with the thermoplastic polymer. Below the phase change temperature of the solvent, the phase change solvent solidifies or crystallizes within the thermoplastic matrix. The phase change behavior of these materials produce blended compositions that exhibit lowered shear viscosity and lowered processing temperature without substantially compromising mechanical properties of the thermoplastic polymer. The present invention also relates to a method of improving the processability of a thermoplastic polymer using the phase change solvent.

3 Claims, 3 Drawing Sheets

FOREIGN PATENT DOCUMENTS

| | | |
|---|---|---|
| JP | 63-227658 A | 9/1988 |
| JP | 2189348 | 7/1990 |
| JP | 2196844 A | 8/1990 |
| JP | 5125240 A | 5/1993 |
| WO | WO 96/05253 | 2/1996 |
| WO | WO 00/11092 | 3/2000 |

OTHER PUBLICATIONS

Chem Abstracts. 1992:21832, "Liquid -crystalline oligoesters containing sinle-ringaromatic units separated by aliphatic spacers" Teng et al. Polymeric Materials Science and Engineering (1991), 65, 33-4.*

Chem Abstracts 1995:976847, "A test of the applicability of small-molecule group additivity parameters in the estimation of fusion entropies of macromolecules" Chickos et al. Thermochimica Acta (1995), 264, 13-26.*

Aldrich Chemical Company catalog, 2005-6.

Sci-Finder search of CAPLUS, MEDLINE, CASREACT and CHEMLIST, CHEMCATS databases on Feb. 3, 2006.

Partial European Search Report dated Jan. 24, 2008, 2 pages.

* cited by examiner

PHASE CHANGE SOLVENTS

CROSS-REFERENCE TO RELATED APPLICATION

This application claims the benefit of U.S. Provisional Application 60/399,963, filed Jul. 31, 2002.

FIELD OF INVENTION

The present invention relates to blended thermoplastic polymer compositions comprising phase change solvents. Above the phase change temperature of the solvent, the phase change solvents solubilize or intimately mix with the thermoplastic polymer. Below the phase change temperature of the solvent, the phase change solvents solidify or crystallize within the thermoplastic polymer matrix. The phase change behavior of the solvents produces polymeric compositions that exhibit lowered viscosity and lowered processing temperature without substantially compromising mechanical properties. The present invention also relates to a process for improving the processability of a thermoplastic polymer using the phase change solvent.

BACKGROUND OF THE INVENTION

Plastic materials are broadly divided into two main classes based on the material's response to heat, thermoplastics and thermosetting resins. Thermoplastic resins, when heated, soften or melt and flow as liquids and when cooled, they solidify. These changes on heating and cooling can be repeated several times without appreciable degradation. Virtually all thermoplastic products are made by melting thermoplastic compounds, shaping the molten plastic, and cooling it while maintaining the shape. In contrast, thermosetting resins are cured, hardened, or "set" into a permanent shape. Curing is an irreversible process whereby permanent crosslinking occurs. Thus once molded, a thermoset product cannot be reheated and molded again.

The majority of resins produced are thermoplastics. Although a number of chemically different kinds of thermoplastics are commercially available, they can be divided into two broad classes: amorphous and crystalline. The latter are characterized by melting and freezing points. Amorphous resins do not have melting points, but rather are defined by a glass transition temperature, Tg. Common amorphous thermoplastics are polystyrene, polycarbonates, poly(methyl methacrylate), and poly(vinyl chloride). Crystalline or partially crystalline thermoplastics are often described by melting temperature and a glass transition temperature. These materials are processed above their melting points and then cooled to cause crystalline domains to form. Examples would include polyethylene, polypropylene, polyethylene terephthalate, and Nylon.

Thermoplastic elastomers are block copolymers having one or more alkenylarene polymer blocks and one or more olefinic polymer blocks. The block copolymers are elastomeric in the sense that they typically have a three-dimensional, entangled (alternatively known as "physically crosslinked") structure below the glass transition temperature ($T_g$) of the alkenylarene block such that they exhibit elastic memories in response to external forces. The block copolymers are thermoplastic in the sense that they can be softened or melted above the glass or crystalline transition temperature of the alkenylarene block, processed, and cooled/solidified several times with little or no change in physical properties (assuming a minimum of oxidative degradation).

Thermoplastics are fabricated into useful shapes and articles using thermal and mechanical processes to manufacture plastic products, articles, films, fibers, or coatings, for example. A particular polymer is usually chosen based on the mechanical, thermal, or visual properties desired in the product. For a particular fabrication process, e.g., extrusion, film blowing, molding, coating, and forming, the process variables (temperatures, flowrates, pressures, scrap, cost, etc.) are typically selected such that the rheological properties of a polymer are adequate. However, the selections of polymer and process are highly related. In certain situations, the polymer may degrade at elevated temperatures or the equipment reliability is unacceptable at high temperatures. Additionally, the theological properties of some polymers may render certain processes or process conditions impossible or non-optimal, which may preclude these polymers from being employed regardless of their mechanical properties.

Plasticizers or processing oils are often added to block copolymers to lower the viscosity and improve the processability of block copolymers. Other polymers may also be added to compatibilize the blends and/or improve the mechanical properties. Blends comprising block copolymers are reportedly described in U.S. Pat. Nos. 3,562,356; 4,704,110; 4,578,302; 5,503,919; 5,540,983; 6,117,176; and 6,187,425. However, the addition of plasticizers and/or processing oils lowers the mechanical properties of the block copolymer compositions.

U.S. Pat. No. 4,131,581 to Coker relates to crystalline solvents for a polymer component that must be miscible with a viscosity reducing diluent. U.S. Pat. No. 5,945,485 to Struglinski et al. relates to viscosity modifier polybutadiene polymers, and U.S. Pat. No. 5,633,319 to Silvi et al. relates to compatibilized blends of polyetherimides and liquid crystalline polyesters, optionally with a minor proportion of a non-liquid crystalline polyester.

The present inventors provide herein phase change solvents that are able to reduce viscosity of a thermoplastic at high temperatures for processing while not substantially compromising the mechanical strength of the polymer at use temperatures.

SUMMARY OF THE INVENTION

The present invention relates to novel thermoplastic polymer/phase change solvent blended compositions wherein the phase change solvent has a phase change in a temperature range from 40° C. to 250° C. The thermoplastic polymer is selected from the group consisting of a block copolymer, a polyester, a polyamide, a polyether, a polyurethane, a polycarbonate, a vinyl polymer, and a mixture thereof. The phase change solvent is selected from a group of general formulas (I) to (X) provided in the detailed description herein. Processes of improving the processability of a thermoplastic polymer comprising blending the polymer with a phase change solvent are aspects of the present invention.

The phase change temperature of the blended compositions can be controlled by molecular characteristics of the phase change solvent, such as the monomeric structure, the molecular weight, the aromatic and aliphatic carbon content in the backbone, or the like. The shear viscosity of the phase change solvent and of the thermoplastic polymer blend can be varied over a broad range to achieve suitable shear viscosity for different fabricating processes. The blended compositions exhibit low shear viscosities, low processing temperatures and good mechanical properties. The blended compositions may be processed by various methods, including extrusion, injection molding, melt spinning, blow molding, printing, spraying, coating, or the like.

The present invention also provides novel phase change solvents having general formulas (I), (II), or (IV-a) where the number of carbons of the monomer repeated unit (Px) is not the same as the number of carbons in the end groups ($P_y$); having general formulas (V), (VI), or (VII) where the number of carbons of the monomer repeated unit (R") is not the same as the number of carbons in the end groups ($P_y$); and having the general formulas (VIII), (IX), or (X) which have repeats (W-R") and inverted repeats (W'-R'") and the number of carbons in the repeat (R") or the inverted repeat (R'") is not the same as the number of carbons in the end groups ($P_y$). Processes of preparing such a novel phase change solvent are also aspects of the present invention.

As used herein and in the claims, the terms "a" and "an" mean "one or more." All documents cited are, in relevant part, incorporated herein by reference; the citation of any document is not to be construed as an admission that it is prior art with respect to the present invention.

DETAILED DESCRIPTION OF THE INVENTION

Figure 1:
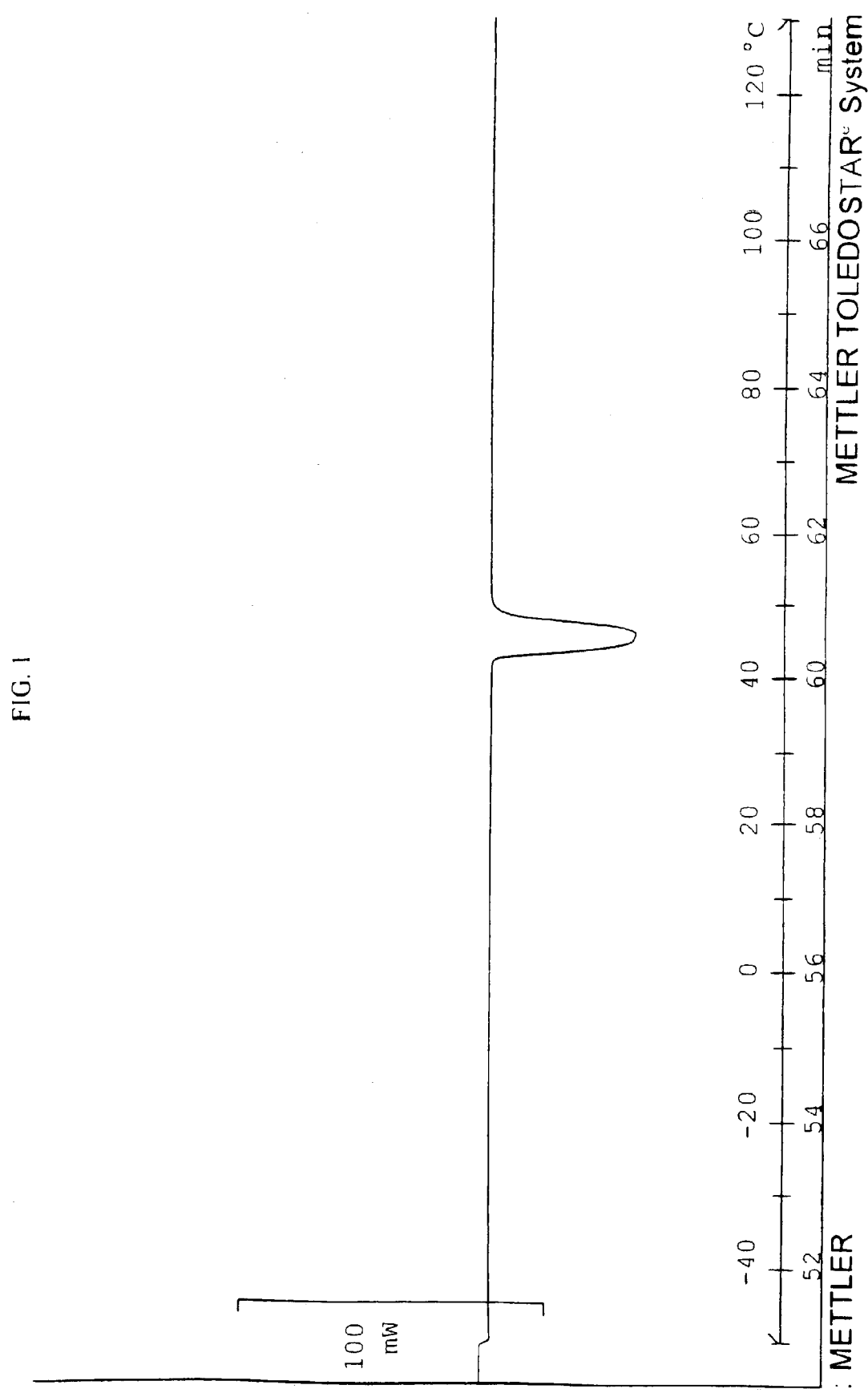
FIG. 1 is a DSC thermogram showing phase change properties of the phase change solvent of Example 1. The y axis or ordinate represents increasing exothermic heat flow.

Phase change solvents useful for the present invention have at least one phase change temperature in the range from 40° C. to 250° C., from 50° C. to 180° C., or from 60° C. to 150° C. The phase change may be a crystalline transition (a first order transition), a glassy transition (a second order transition), a liquid crystalline transition, or a combination thereof. A phase change solvent may have one or more phase changes. The definitions of these phase changes can be found in *Principles of Polymer Chemistry*, by Flory, Cornell University Press (1953) and *Liquid Crystals*, by Chandrasekhar Cambridge University Press, 1992. The phase changes may be characterized by standard techniques, such as Differential Scanning Calorimetry (DSC), Differential Thermal Analysis (DTA), and the like.

Phase change solvents may be a low molecular weight resin or oligomer having one or more low phase change temperatures. Further, a phase change solvent may have a structure that is similar to the structure of some thermoplastic polymers so that the phase change solvent will intimately mixed with the thermoplastic polymer. The phase change solvent, when blended with a thermoplastic polymer, provides for more flexible processing conditions and/or processing conditions over a broader processing temperature range than that of the polymer absent the solvent. The phase change solvent also may improve mechanical properties, such as tensile and elastic properties, of the blended composition in the temperature range below its phase transition temperature.

As used herein, the term "thermoplastic" refers to any material which can be melted and re-solidified with little or no change in physical properties (assuming a minimum of oxidative degradation).

Phase Change Solvents for Blending with Thermoplastic Polymers

A phase change solvent having a phase change in a temperature range from 40° C. to 250° C. for blending with a thermoplastic polymer to form a blended composition of the present invention has one of the following structures:

  (I)

  (II)

  (III)

  (IV-a)

  (IV-b)

  (V)

  (VI)

  (VII)

  (VIII)

  (IX)

  (X)

For formulas (I)-(IV-b), Q is a substituted or unsubstituted difunctional aromatic moiety. Exemplary Q groups are terephthalic, naphthalic, phenolic, phenyl, or biphenyl or mixtures thereof. P is $CH_2$; R and R' may be the same or different and are independently selected from the group consisting of H, $CH_3$, COOH, $CONHR_1$, $CONR_1R_2$, $NHR_3$, $NR_3R_4$, hydroxy, and C1-C30 alkoxy; wherein $R_1$, $R_2$, $R_3$ and $R_4$ are independently H or linear or branched alkyl from C1-C30; x is an integer from 1 to 30; y is an integer from 1 to 30; and n is an integer from 1 to 7. Q may be substituted on the aromatic ring with one or more substituents selected from the group consisting of H, C1-C30 alkyl, COOH, $CONHR_5$, $CONR_5R_6$, $NHR_7$, $NR_7R_8$, hydroxy, C1-C30 alkoxy, $SO_3H$, and halogen; wherein $R_5$, $R_6$, $R_7$ and $R_8$ are independently H or linear or branched alkyl from C1-C30.

An example of a solvent having formula III is:

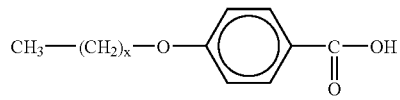

An example of a solvent having formula (I) is as follows:

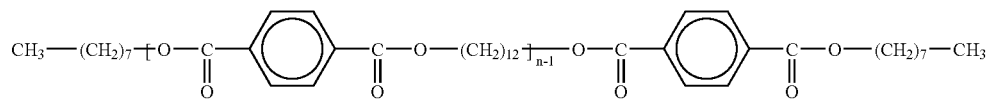

For formulas (V)-(VII), W is selected from the group consisting of —C(=O)—O—, —O—C(=O)—, —O—C(=O)—O—, —C(=O)—NH—, —NH—C(=O)—, imide, —O—, —NR$_9$—C(=O)—O—, and —NR$_9$—C(=O)—NR$_{10}$—, wherein R$_9$ and R$_{10}$ are independently H or linear or branched alkyl from C1-C30; P is CH$_2$; R and R' may be the same or different and are independently selected from the group consisting of H, CH$_3$, COOH, CONHR$_1$, CONR$_1$R$_2$, NHR$_3$, NR$_3$R$_4$, hydroxy, and C1-C30 alkoxy; wherein R$_1$, R$_2$, R$_3$ and R$_4$ are independently H or linear or branched alkyl from C1-C30; R" is linear or branched C1-C30 alkyl; y is an integer from 0 to 30, preferably, from 1-30; and n is an integer from 1 to 7. Examples of solvents having formula (V) are as follows.

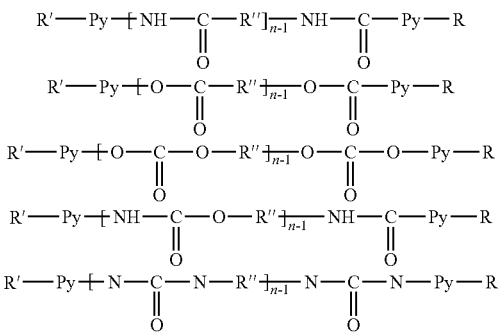

For formulas (VIII)-(X), W and W' are independently selected from the group consisting of —C(=O)—O—, —O—C(=O)—, —O—C(=O)—O—, —C(=O)—NH—, —NH—C(=O)—, imide, —O—, —N R$_9$-C(=O)—O—, —O—C(=O)—NR$_9$—, —NR$_9$—C(=O)—NR$_{10}$—, and —NR$_{10}$—C(=O)—NR$_9$—; wherein when W and W' are the same, R" and R'" are not the same; and wherein R$_9$ and R$_{10}$ are independently H or linear or branched alkyl from C1-C30; P is CH$_2$; R and R' may be the same or different and are independently selected from the group consisting of H, CH$_3$, COOH, CONHR$_1$, CONR$_1$R$_2$, NHR$_3$, NR$_3$R$_4$, hydroxy, and C1-C30 alkoxy; wherein R$_1$, R$_2$, R$_3$ and R$_4$ are independently H or linear or branched alkyl from C1-C30; R" and R'" are independently linear or branched C1-C30 alkyl; y is an integer from 0 to 30, preferably, from 1-30; and n is an integer from 1 to 7. A mixture of any of the above solvents having formulas (I)-(X) blended with a thermoplastic polymer is also contemplated by the present inventors. An example of a solvent having formula (VIII) is as follows where x' is an integer from 1 to 30.

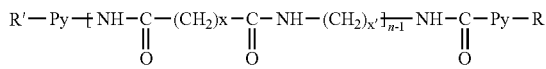

The phase change solvents of the present invention have a number-average molecular weight from about 150 to about 5000, from about 500 to about 3000, or from about 800 to about 2500. Higher molecular weight materials typically exhibit higher phase change temperatures, which may not effectively lower the processing temperatures and/or viscosities of the thermoplastic polymer. Moreover, higher molecular weight materials may not be effective in solubilizing the thermoplastic polymer, that is, they may not mix intimately with the polymer. Low molecular weight materials, when blended with thermoplastic polymers, may function more like traditional plasticizers, processing oils, or other viscosity additives. That is, they may lower the mechanical properties of the resulting composition.

The effectiveness of a phase change solvent having formula (I)-(IV-b) is related to the AA ratio, which is defined as follow:

AA ratio=$C_{aliphatic}/C_{aromatic}$ wherein $C_{aliphatic}$ is the number of aliphatic carbons (excluding those aliphatic carbons that may be present in the substituents) of the P units in the formula, and $C_{aromatic}$ is the number of aromatic carbons (excluding any aromatic carbons that may be present in the substituents) in the Q units of the formula. For example:

$C_{aliphatic}$=#P$_y$ groups*y+# repeat units*x+#C in R+# C in R'; and $C_{aromatic}$=n*6 (if the Q unit is terephthalic, phenolic or phenyl), or $C_{aromatic}$=n*10 (if the Q unit is naphthalic or biphenyl).

A phase change solvent having formula (I)-(IV-b) has an AA ratio from about 0.25 to about 4, from about 1.0 to about 3.5, from about 1.5 to 2.7, or from about 2.0 to about 2.6. Moreover, in some embodiments, the AA ratio of the phase change solvent may be substantially the same as that of the thermoplastic polymer in the compositions. It is found that compositions containing phase change solvent and thermoplastic polymer with similar AA ratios exhibit better mechanical properties. The difference in AA ratio between the phase change solvent and thermoplastic polymer may have an absolute value of less than about 1.5, less than about 1, or less than about 0.5.

The effectiveness of a phase change solvent having formula (V)-(X) is related to the AP ratio, which is defined as follow:

AP ratio=$C_{aliphatic}$/number of polar groups wherein $C_{aliphatic}$ is the number of aliphatic carbons (excluding those aliphatic carbons that may be present in the substituents) of the P units plus the number of aliphatic carbons in R"+R'" in the formula, and the number of polar groups is the number of W groups plus the number of W' groups. W and W' are defined supra. For example:

$C_{aliphatic}$=#P$_y$ groups*y+# repeat units*# C in R"+# repeat units*#C in R'"+#C in R+# C in R'; and Number of polar groups for formulas (VI) and (IX)= #W*n+# W'*n; or Number of polar groups for formulas (V), (VII), (VIII), or (X)=#W*(n-1)+# W'*(n-1).

A phase change solvent having formula (V)-(X) has an AP ratio from 1 to 30, from 1 to 25, from 1-15, from 1-10, or from 1-5, for example. Moreover, in some embodiments, the AP ratio of the phase change solvent may be substantially the same as that of the thermoplastic polymer in the compositions. It is found that compositions containing phase change solvent and thermoplastic polymer with similar AP ratios exhibit lower shear viscosity. The difference in AP ratio between the phase change solvent and thermoplastic polymer may have an absolute value of less than about 1.5, less than about 1, or less than about 0.5.

The synthesis of solvents having structures (I)-(X) is based on condensation type polymer chemistry. Structures include amides, carbonates, esters, imides, ureas and urethanes. A general example is the reaction of a diacid chloride with a diol. A polyester is generated and hydrochloric acid is a byproduct. The molecular weight of the oligomer can be controlled via using an excess of one the reactants to produce a low molecular weight oligomer whose end groups are that of the monomer in excess. Further, the molecular weight can be limited and the end group functionality changed via use of a monofunctional reagent of a type which can react with the end groups resulting from the difunctional monomer in excess. For example, if a diacid chloride is used in excess, an oligomer with carboxylic acid type end groups is obtained. If, to this same recipe, a monofunctional alcohol is added in an amount equal to the excess of acid chloride end groups then an oligomer with alkyl chain end groups can be obtained where both the molecular weight and end group structures are controlled.

The synthesis of solvents having structures (I)-(IV-b) is based on aromatic structures with amide, carbonate, ester or ether linkages. These may be prepared by various methods, which include the reaction of carboxylic acids, acid halides, anhydrides or isocyanates with alcohols or amines.

The synthesis of solvents having structures (V) thru (X) are based on amide, carbonate, ester, ether, urea or urethane linkages. Acid chloride reactions with alcohols or amines occur at room temperature while reactions of acids or esters directly with alcohols or amines require considerable heat and/or catalyst additions to carry out. Such reaction conditions are known to one of skill in the art in light of the present disclosure. The reactions of isocyanates with alcohols or amines can be carried out under mild conditions and may be accelerated by addition of catalysts.

Novel Phase Change Solvents

The present invention provides novel phase change solvents having a phase change in a temperature range from 40° C. to 250° C. Such a solvent is a composition comprising a phase change solvent having the general formula (I), (II), or (IV-a) wherein Q, P, R and R' are as set forth above; x and y are independently an integer from 1 to 30, and x≠y; n is an integer from 1 to 7 when the solvent has the formula (II); and n is an integer from 2 to 8 when the solvent has the formula (I) or (IV-a).

A process for preparing such a new phase change solvent having formula (I) or (II) and as set forth in the preceding paragraph comprises combining A) a monofunctional aliphatic alcohol or monofunctional aliphatic amine having y carbons; B) a difunctional aromatic diacid, difunctional aromatic acid salt, difunctional aromatic ester, or difunctional aromatic isocyanate; and C) a difunctional aliphatic diol or a difunctional aliphatic diamine having x carbons; in a molar ratio of A:B:C of 2:n:n-1 where 2≦n≦8 and under conditions to produce the phase change solvent having formula (I); or in a molar ratio of A:B:C of 1:n:n where 1≦n≦7) and under conditions to produce the phase change solvent having formula (II).

A process for preparing a novel phase change solvent having formula (I) or (IV-a) as set forth hereinabove comprises combining D) a monofunctional aliphatic acid, monofunctional aliphatic acid salt, monofunctional aliphatic ester, or monofunctional aliphatic isocyanate; E) a difunctional aromatic diol, or difunctional aromatic diamine; and F) a difunctional aliphatic diacid, difunctional aliphatic acid salt, difunctional aliphatic ester, or difunctional aliphatic isocyanate having x carbons; in a molar ratio of D:E:F of 2:n:n-1 where 2≦n≦8 and under conditions to produce the phase change solvent having formula (I); or in a molar ratio of D:E:F of 1:n:n-1 where 2≦n≦8 and under conditions to produce the phase change solvent having formula (IV-a).

A further novel composition comprises a phase change solvent having the general formula (V), (VI), or (VII), wherein W, P, R and R' are as set forth above, R" is linear or branched C1-C30 alkyl and R"≠$P_y$; y is an integer from 1 to 30; n is an integer from 1 to 7 when the solvent has the formula (VI); and n is an integer from 2 to 8 when the solvent has the formula (V) or (VII).

A process for preparing the novel phase change solvent having formula (V) or (VI) as set forth in the preceding paragraph comprises combining A) a monofunctional aliphatic amine having y carbons; B) a difunctional di-isocyanate; and C) an aliphatic difunctional diamine having x carbons; in a molar ratio of A:B:C of 2:n:n-1 where 2≦n≦8 and under conditions to produce the phase change solvent having formula (V); or in a molar ratio of A:B:C of 1:n:n where 1≦n≦7 and under conditions to produce the phase change solvent having formula (VI).

A process for preparing a novel phase change solvent having formula (V) or (VII) as set forth hereinabove comprises combining D) a monofunctional aliphatic acid salt having y carbons; E) a difunctional diol; and F) phosgene; in a molar ratio of D:E:F of 2:n:n-1 where 2≦n≦8 and under conditions to produce the phase change solvent having formula (V); or in a molar ratio of D:E:F of 1:n:n-1 where 2≦n≦8 and under conditions to produce the phase change solvent having formula (VII).

A process for preparing a novel phase change solvent having formula (V) or (VII) as set forth hereinabove comprises combining G) a monofunctional aliphatic isocyanate having y carbons; H) a difunctional diamine; and I) a difunctional aliphatic di-isocyanate having x carbons; in a molar ratio of G:H:I of 2:n:n-1 where 2≦n≦8 and under conditions to produce the phase change solvent having formula (V); and in a molar ratio of G:H:I of 1:n:n-1 where 2≦n≦8 and under conditions to produce the phase change solvent having formula (VII).

A process for preparing a novel phase change solvent having formula (V) or (VI) as set forth hereinabove comprises combining J) a monofunctional aliphatic alcohol having y carbons; K) phosgene; and L) a difunctional aliphatic diol having x carbons; in a molar ratio of J:K:L of 2:n:n-1 where 2≦n≦8 and under conditions to produce the phase change solvent having formula (V); or in a molar ratio of J:K:L of 1:n:n where 1≦n≦7 and under conditions to produce the phase change solvent having formula (VI).

Another novel composition of the present invention comprises a phase change solvent having the general formula (VIII), (IX), or (X) wherein W, W', P, R, R', R", and R''' are as set forth above, and when R"=Py, R'''≠Py; when R"≠Py, R''' may be the same as or different than Py; y is an integer from 1 to 30; n is an integer from 1 to 7 when the solvent has formula (IX); and n is an integer from 2 to 8 when the solvent has formula (VIII) or (X).

A process for preparing a novel phase change solvent having formula (VIII) or (IX) of the preceding paragraph comprises combining A) a monofunctional aliphatic alcohol or monofunctional aliphatic amine having y carbons; B) a difunctional diacid, difunctional acid salt, difunctional ester, difunctional isocyanate, or difunctional phosgene; and C) a difunctional aliphatic diol or difunctional aliphatic diamine having x carbons; in a molar ratio of A:B:C of 2:n:n-1 where 2≦n≦8 and under conditions to produce the phase change solvent having formula (VIII); or in a molar ratio of A:B:C of 1:n:n where 1≦n≦7 and under conditions to produce the phase change solvent having formula (IX).

A process for preparing a novel phase change solvent having formula (VIII) or (X) as set forth hereinabove comprises combining D) a monofunctional aliphatic acid, monofunctional aliphatic acid salt, monofunctional aliphatic ester, or monofunctional aliphatic isocyanate; E) a difunctional diol, or difunctional diamine; and F) a difunctional aliphatic diacid, difunctional aliphatic acid salt, difunctional aliphatic ester, difunctional aliphatic isocyanate, or phosgene; in a molar ratio of D:E:F of 2:n:n-1 where $2 \leq n \leq 8$ and under conditions to produce the phase change solvent having formula (VIII); and in a molar ratio of D:E:F of 1:n:n-1 where $2 \leq n \leq 8$ and under conditions to produce the phase change solvent having formula (X).

A phase change solvent having a phase change in a temperature range from 40° C. to 250° C. and, when blended with a thermoplastic polymer at 20% solvent and 80% polymer, the blend having a shear viscosity less than 50% of a shear viscosity of the thermoplastic polymer absent the phase change solvent, and having a tensile strength at least 70% of a tensile strength of the thermoplastic polymer absent the phase change solvent is an aspect of the present invention. Shear viscosity is measured at a temperature of 50° above a softening point of the polymer, and tensile strength is measured at ambient temperature.

Thermoplastic Polymers for Blending with Phase Change Solvents

Thermoplastic polymers for blending with phase change solvents of the present invention are selected from the group consisting of a block copolymer, a polyester, a polyamide, a polyether, a polyurethane, a polycarbonate, a vinyl polymer, and a mixture thereof.

Block copolymers have one or more alkenylarene polymer blocks and one or more olefinic polymer blocks. The block copolymers are elastomeric in the sense that they typically have a three-dimensional, entangled (alternatively known as "physically crosslinked") structure below the glass transition temperature ($T_g$) of the alkenylarene block such that they exhibit elastic memories in response to external forces. The block copolymers are thermoplastic in the sense that they can be softened or melted above the glass or crystalline transition temperature of the alkenylarene block, processed, and cooled/solidified several times with little or no change in physical properties (assuming a minimum of oxidative degradation). The polyalkenylarene block is derived from monomers such as styrene, α-methyl styrene, para-methyl styrene, other alkyl styrene derivatives, or mixtures thereof, or a copolymer derived from alkenylarene monomers and short C2-C6 alkene monomers such as ethylenes, propylenes, butylenes; C2-C6 diene monomers such as isoprenes, butadienes; or mixtures of alkene/diene monomers. The olefinic block may be a diene polymer derived from unsaturated or partially saturated diene monomers of from about 4 to about 6 carbons. Suitable diene monomers may include butadiene, isoprene, and the like. The olefinic block may also be an olefinic polymer derived from linear or branched alkene monomers of from about 2 to about 6 carbon atoms. Suitable alkene monomers may include ethylene, propylene, butylene, and the like. The olefinic block may also comprise a combination of the above monomers, such as ethylene/propylene polymers, ethylene/butylene polymers, and the like.

Polyamides are often referred to as nylons and the terms have become synonymous. Nylons are designated commercially with a numbering system that indicates the number of carbon atoms in the monomer unit. Nylons made from aminoacids are designated by 1 number, e.g., Nylon 6 is the common name for poly(w-aminocaproic acid). Nylons that are synthesized from the reaction of a diacid and diamine are designated with 2 numbers, one referring to the diamine and the second indicating the acid. For example, Nylon 6-6 is synthesize from hexamethylenediamine and adipic acid and Nylon 6-10 is made from hexamethylenediamine and sebacic acid. The properties of nylons as plastic articles and fibers are characterized by a combination of high strength, elasticity, toughness, and abrasion resistance at low temperatures. The materials are partially crystalline, with melting points in the range of 150-250° C. and glass transition temperatures in the 60-70° C. range. The excellent properties are maintained up to temperatures of 150° C. A large fraction of nylons are used in household carpeting, apparel fabrics, and engineering uses such as bearings and gears.

Polyurethanes are typically synthesized by reacting a diisocyanate and a diol. Polymers that result from this reaction are useful in products such as foams, elastomers, fibers, and coatings. Practically all polyurethane foams are crosslinked, and hence are thermosets and fall outside the scope of thermoplastic polyurethanes of the present invention. Polyurethane elastomers are made in a several step process that involves a basic intermediate which is reacted with a diisocyanate to yield a prepolymer. The prepolymer is then reacted with diamines, diacids, or amino alcohols to produce larger molecular weight materials that possess hard and soft blocks, as described in the block copolymer section above. Polyurethane elastomers are known for their good elasticity, abrasion resistance, hardness and resistance to solvents. Polyurethanes are also often used as coatings and provide excellent solvent resistance, and abrasion resistance. In addition the materials can be made into fibers with excellent elastic properties for fabrics, gathers, and waistbands.

Polyesters are made from reacting diacids with diols. Their synthesis techniques are similar to that of polyamides, although the reaction equilibrium is less favorable. However, techniques have been developed in the industry to circumvent much of the equilibrium issues, e.g., ester inter-change reactions are carried out. One of the most common polyesters is known as polyethylene terephthalate, PET, which is a crystalline thermoplastic having melting points and glass transitions in the 240-260° C. and 70-80° C. ranges, respectively. Owing to their superior strength, impact resistance, and toughness, polyesters are commonly formed into fibers, films, and bottles. Polyester fibers are often blended with other fibers to create fabric that have less wrinkling, and can easily be laundered. Polyester cords are often used in tire cord. PET bottles are the standard for soft drinks and is the primary use of the material.

Polyethers are polymers that consist of the group R—O—R—O in the chain structure. They are often made from ring-opening polymerizations of ethylene oxide or trioxane. Polymers resulting from the trioxane polymerization are often referred to as Acetal resins and the melting points are typically in the 170-190° C. range with high degrees (>75%) of crystallinity. Often these polymers are used as direct replacements for metals, because their impact strength, stiffness, light weight and resistance to wear approaches or exceeds many metallic materials. Those deriving from ethylene oxide also are highly crystalline, with adequate mechanical properties but also can be water soluble.

Polycarbonates are typically synthesized from the reaction of phosgene and bis-phenol A or by the ester exchange between bisphenol A and diphenyl carbonate. Polycarbonate is a crystalline thermoplastic and has outstanding mechanical properties such as impact resistance. It is often employed in injection molded or extruded products, such as telephone parts, business equipment housing, auto tail-light lenses.

Vinyl polymers are a large class of materials having the general structure:

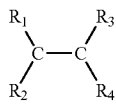

where R1, R2, R3, R4 can be H, halogen, aromatic, aliphatic, ester, ether, or hydroxyl, for example. Typically, R1, R2, R3 are unsubstituted and R4 is employed as the functionality. For this class of polymers, the properties vary widely among the members in this class, depending on the substituents. The polymers in vinyl class can display widely varying properties, ranging from elastomeric to brittle solids (and virtually anything in between) depending on the selection of substituents. Examples of vinyl polymers are polyethylene or polypropylene, for example; a styrenic such as polystyrene, poly(alpha-methyl styrene), or poly(tert-butyl styrene), for example; an acrylic such as poly(methylmethacrylate), poly(butyl acrylate), for example; a polyvinyl halide such as poly(vinyl chloride), poly(tetrafluoroethylene) aka TEFLON, or poly(vinylidene chloride), for example; a poly(vinyl alcohol); or a poly(vinyl acetate), for example.

Thermoplastic Polymer/Phase Change Solvent Blended Compositions

A composition comprising from 1 to 99 wt % of a thermoplastic polymer selected from the group consisting of a polyester, a polyamide, a polyether, a polyurethane, a polycarbonate, a vinyl polymer, and a mixture thereof; and from 1 to 70 wt % of a phase change solvent having the general formula (I), (II), (III), (IV-a), (IV-b), or a mixture thereof is an embodiment of the present invention. A further embodiment of the invention is a composition comprising from 1 to 99 wt % of a thermoplastic polymer selected from the group consisting of a block copolymer, a polyester, a polyamide, a polyether, a polyurethane, a polycarbonate, a vinyl polymer, and a mixture thereof; and from 1 to 70 wt % of a phase change solvent having the general formula (V), (VI), (VII), (VIII), (IX), or (X), or a mixture thereof.

Another embodiment of the present invention is a thermoplastic polymer/phase change solvent blended composition comprising from 1 to 99 wt % a thermoplastic polymer selected from the group consisting of a polyester, a polyamide, a polyether, a polyurethane, a polycarbonate, a vinyl polymer, and a mixture thereof; and from 1 to 70 wt % a phase change solvent wherein the phase change solvent has a phase change in a temperature range from 40° C. to 250° C. For this embodiment, when blended at 20% solvent and 80% polymer, the composition has a shear viscosity less than 50% of a shear viscosity of the thermoplastic polymer absent the phase change solvent, and has a tensile strength at least 70% of a tensile strength of the thermoplastic polymer absent the phase change solvent. Shear viscosity is measured at a temperature of 50° above a softening point of the polymer, and tensile strength is measured at ambient temperature. Ambient temperature as used herein means about room temperature, 20° C. to 25° C. For some embodiments of the present invention, the blended composition has improved modulus or improved extension as compared to modulus or extension of the thermoplastic polymer absent the phase change solvent.

In further embodiments of the invention, the phase change solvent is present in the blended composition in an amount from about 1 to about 70 weight percent, from about 10 to about 60 weight percent, or from about 20 to about 50 weight percent, of the blended composition.

The thermoplastic polymer may be present in the blended composition in an amount effective to achieve the desired mechanical properties, such as tensile, elastic and stress relaxation properties. The thermoplastic polymer may be present in the blended composition in an amount from about 1 to about 99 weight percent, from about 20 to about 80 weight percent, or from about 30 to about 70 weight percent, of the composition.

The phase change solvent changes the shear viscosity of the thermoplastic polymer. In the range of its phase change temperature, the phase change solvent may effect a rapid change in shear viscosity of the polymer. A change in shear viscosity renders the blended compositions processable at a temperature much lower than the typical melt processing temperature of the neat thermoplastic polymer. Because of the lower processing temperature, substrates with lower thermal stability (e.g., polyethylene and the like) and or delicate structures (e.g., nonwoven webs and the like) may be used.

Moreover, the phase change solvents may be used as shear viscosity modifiers in thermoplastic polymeric compositions to achieve a wide range of viscosities so that the compositions may be suitable for various processes. Compositions not previously considered suitable for processes that operate at low shear viscosity and/or low temperature, such as gravure printing, flexographic printing, ink jet printing, spraying, coating and the like, due to their high viscosities at the processing temperature of the equipment, are made available for processing by the present invention. Styrenic block copolymer compositions are generally considered not suitable for low viscosity processes, for example. Prior to the present invention, volatile solvents and/or high temperature were used to reduce the viscosity of unsuitable polymers. The present invention uniquely provides "volatile solvent-less" (i.e., no volatile solvents) compositions that may be useful in these processes at an operable processing temperature of the equipment.

Further, the phase change solvents of the present invention uniquely modify the shear viscosity of a thermoplastic polymer without substantially compromising the mechanical properties of the polymer. It is well known that plasticizers, viscosity modifiers, and processing oils may be used to lower the viscosity and improve the melt processability of thermoplastic polymers. However, due to their low molecular weight and their softness and/or fluidity down to room temperature, these agents tend to reduce the mechanical properties of the polymers. In contrast, the phase change solvents of the present invention are solid-like at or below room temperature. Thus, in one aspect, they may function like reinforcing particles (i.e., fillers) in the blends. Moreover, the phase change solvents, due to their chemical structures and molecular weights, may be intimately mixed with the thermoplastic polymers, and function as a compatibilizer. When they solidify, the solvents are expected to be fairly homogeneously dispersed throughout the polymer matrix. Homogeneous distribution of reinforcing particles are desirable since fewer stress concentration spots (detrimental to mechanical properties) are created in such structures. The compatibilizing function is also expected to lead to reduced phase sizes and reduced stress concentrations at the interfaces between the phases of the blended compositions.

The shear viscosity of the compositions, measured at a temperature of 50° above a softening point of the polymer of the blend, and at 1 sec.$^{-1}$ shear rate, may be from about 0.1 Pa-s to about 10,000 Pa-s. Because the blended compositions of the present invention provide a broad range of viscosities, they are processable by a wide variety of processes. In some embodiments useful for printing or spraying, the compositions of the present invention may have melt viscosities ranging from about 1 to about 8000 Pa s, from about 5 to about 5000 Pa s, or from about 10 to about 1000 Pa s.

Since the phase change solvents lower the shear viscosity of the compositions of the present invention, embodiments of the present invention may be processed at a temperature more advantageous for processing as compared to compositions absent the solvent.

Some embodiments of the present invention may have a room temperature tensile strength (or normalized load) at 30% strain of at least about 10 newtons/meter, preferably at least about 30 newtons/meter, and more preferably at least about 50 newtons/meter. In other embodiments, the compositions of the present invention may have a room temperature tensile strength (or normalized load) at 200% strain of at least about 100 newtons/meter, preferably at least about 120 newtons/meter, and more preferably at least about 150 newtons/meter. In some embodiments, the compositions of the present invention may have a room temperature tensile strength in the range of from about 10 to about 500 newtons/meter. In some embodiments, the compositions of the present invention may also have a room temperature stress relaxation at 200% elongation of less than about 50%, less than about 35%, or less than about 20% at room temperature.

Optional Ingredients for Blended Compositions

Various processing oils may also be used in the present compositions in the amount from about 1 to about 70 wt %, from about 5 to about 60 wt %, from about 10 to about 50 wt %, or from about 20 to about 40 wt %. Exemplary oils include mineral oil or other petroleum-derived oils or waxes, such as parafinic oil, naphthenic oil, petrolateum, microcrystalline wax, paraffin or isoparaffin wax. Synthetic waxes, such as Fischer-Tropsch wax; natural waxes, such as spermaceti, carnauba, ozokerite, beeswax, candelilla, paraffin, ceresin, esparto, ouricuri, rezowax; and other known mined and mineral waxes, are also suitable for use herein. Olefinic or diene oligomers and low molecular weight polymers may also be used herein. The oligomers may be polypropylenes, polybutylenes, hydrogenated isoprenes, hydrogenated butadienes, or the like having a weight average molecular weight between about 350 to about 8000.

Various nucleating agents may be used in the present compositions. The nucleating agent may induce a phase change of the phase change solvent. The nucleating agent may also increase the crystallization or solidification rate of the phase change solvent and/or the composition. The nucleating agents may be inorganic or polymeric. The inorganic nucleating agent may be an inert particulate such as talc, silica, carbon black, clay, metal oxides (e.g., $TiO_2$), metal carbonates (e.g., $CaCO_3$), or combinations thereof. In some embodiments, the inorganic nucleating agent may be incorporated in the amount from about 0.1 to about 2 wt %.

A polymeric nucleating agent may be a high molecular weight polymer. In some embodiments, the polymer nucleating agent may have one of structures (I)-(X), and a number average molecular weight greater than about 5000. In other embodiments, a suitable polymeric nucleating agent may have one of structures (I)-(X), with y ranging from 8 to 30 and n being 7 or greater. Such high molecular weight polymers are not useful as phase change solvents because their phase change temperatures may be near or higher than the processing temperature such that they remain solid at the processing temperature. In some embodiments, the polymeric nucleating agents are present in an amount from about 0.01 to about 20 wt %, preferably from about 0.05 to about 10 wt %, and more preferably from about 0.1 to about 2 wt %.

Even in the absence of optional nucleating agents disclosed above, the phase change solvents may exhibit a "self-nucleating" behavior. That is, upon cooling, higher molecular weight phase change solvent molecules crystallize or solidify first, and serve as nuclei for lower molecular weight phase change solvent molecules.

Other additives may be incorporated into the present compositions include stabilizers and/or anti-oxidants, dyes, pigments, fillers, anti-blocking agents, flame retardants, and the like.

Uses of Thermoplastic Polymer/Phase Change Solvent Blended Compositions

The blended compositions of the present invention may be processed by various methods, including extrusion, injection molding, melt spinning, blow molding, printing, spraying, coating, fiber spinning, cast or blown films, or the like. The blended compositions may be used as a delivery vehicle for colorants, especially for producing durable colors. The blended polymers may be applied to adhere to fabric, for example, by spray printing or dipping.

Traditional extrusion processes produce sheets or strands of polymeric materials. Subsequent cutting of the polymeric sheets or strands to the desired size and/or shape and joining the cut pieces to a substrate are typically required. Overall, the above processes involve multiple steps to produce the finished product and generate a lot of wasted materials. In view of these drawbacks, the ability to print or spray thermoplastic polymer/phase change solvent blended compositions is particularly advantageous. The printing and spraying processes are able to deliver the thermoplastic materials directly onto the substrate, thus, avoiding the drawback of a multi-step process. These processes are also able to deliver the thermoplastic polymer/phase change solvent blended composition only to targeted areas where they are needed, thus, minimizing the amount of waste generated. Moreover, these processes are able to provide controlled delivery of varying amounts of blended compositions to discrete areas in a single step, which is difficult, if not impossible, to achieve by traditional extrusion/molding processes.

Magnetic particles may be added to a blended composition of the present invention, or a phase change solvent may be added to a magnetic composition to lower viscosity. Magnetic compositions may be applied to substrates to form mating/engaging elements of closure or fastening means, such as closure or fastening means used in resealable bags such as "Ziploc®"-type bags, boxes such as wipe dispensers, absorbent articles, garments, or footware in place of VELCRO, for example.

A process of improving the processability of a thermoplastic polymer for any of such uses is an aspect of the present invention. The thermoplastic polymer is selected from the group consisting of a block copolymer, a polyester, a polyamide, a polyether, a polyurethane, a polycarbonate, a vinyl polymer, and a mixture thereof. The process comprises blending the thermoplastic polymer in an amount of from 1 to 99 wt % and a phase change solvent in an amount of from 1 to 70 wt % to form a blend, the phase change solvent has the general formula (V), (VI), (VII), (VII), (IX), (X), or a mixture thereof; wherein the phase change solvent has a phase change in a temperature range from 40° C. to 250° C., and wherein the processability of the blend is improved compared with processability of the polymer. A process of improving the processability of a thermoplastic polymer as defined above, other than a block copolymer, is an aspect of the present invention and, for this embodiment, the phase change solvent has the general formula (I), (II), (III), (IV-a), (IV-b), or a mixture thereof. Products of such processes are also contemplated by the present inventors as aspects of their invention.

Blended compositions of the present invention are suitable for use in any application where thermoplastic polymers are used. Such uses are well known to one of skill in the art in light of the present disclosure. In particular, blended compositions having block copolymers are suited for elastic components of disposable articles, such as taped or fastened diapers, training pants, pull-on diapers, adult incontinence products, bandages, wraps, wound dressings, surgical drapes, and the like. The elastic components may be portions of the absorbent article, such as the waistbands, leg cuffs, side panels, stretch ears, topsheet, and outer cover, that provide a body-conforming function, a restraint function, or other functions of the disposable article when it is worn. The compositions may also be used as stretchable woven or nonwoven fabric in durable articles, stretch garments including sports wear, swimwear, socks, undergarments, medical garments or devices, and the like.

Blended compositions provided by the present invention are useful for films and laminates. A film or laminate may be employed in a variety of disposable products including, but not limited to, disposable diapers, shrink-wrapping (e.g., food wraps, consumer product wraps, pallet and/or crate wraps, and the like), or bags (grocery bags, food storage bags, sandwich bags, resealable "Ziploc®"-type bags, garbage bags, and the like). The film may be a liquid impervious backsheet or a perforated topsheet suitable for use in absorbent disposable sanitary garments such as disposable diapers, feminine hygiene products or the like.

All percentages, ratios and proportions used herein are defined by weight of the composition unless otherwise specified.

Test Methods

A. Differential Scanning Calorimetry (DSC)

DSC is a well known method for thermal measurements. This method is capable of determining the temperature ranges at which the phase changes of materials occur. Here, the phase change temperatures are useful in selecting the phase change solvents and correlating with the processability and mechanical properties of the thermoplastic polymer blended compositions containing them.

The measurements are performed using a Model 822 DSC from Mettler, Columbus, Ohio or a System 7 DSC from Perkin-Elmer, Shelton, Conn. The instrument is interfaced with a computer for controlling the heating/cooling rates and other test parameters, and for collecting, calculating and reporting the data. The test procedure follows that of ASTM D3418 generally. The procedure is as follows:

(1) calibrate the instrument according to the manufacture's instructions;
(2) a sample material (ca. 15 mg) is placed into aluminum pans, capped, crimped and placed into the instrument according to manufacturer's instructions;
(3) if testing a new material, it may be necessary to perform one or more trial scans to determine an appropriate temperature range for the measurements, which should provide sufficient baseline before and after the observed transition; a typical temperature scan ranges from −50° C. to about 50° C. above the highest phase transition temperature of the sample being tested; for the phase change solvents of the present invention, a typical DSC scan ranges from −50° C. to 200° C.;
(4) program the instrument as follows: the sample temperature is set to the lower limit of desired test range; the temperature is held at the lower limit for 5 minutes and then it is increased at a rate of 10° C./min until reaching the upper limit; the temperature is held at the upper limit for 5 minutes and then the sample is cooled to the lower limit at 10° C./min; the temperature is held at the lower limit for 5 minutes and then the sample is heated at 10° C./min to the upper limit for a second heating scan;
(5) start the test and collect data simultaneously.

The results (including onset temperature, the peak temperature, the heat of phase transition) from the second heating scan are reported.

B. Tensile Strength and Elongation at Failure

The properties determined by this method are expected to correlate with the utility of the blended thermoplastic/phase change solvent compositions provided herein. These properties are relevant to the choice of material suitable for use as the plastic component of an absorbent article, a film, fiber, or molded article, for example.

A commercial tensile tester from Instron Engineering Corp., Canton, Mass. or SINTECH-MTS Systems Corporation, Eden Prairie, Minn. may be used for this test. The materials are pressed to a desired thickness (ca. 0.005") with a hydraulic press, available from Carver Inc, Wabash, Ind. at temperatures depending on the thermoplastic, ranging from 175° C. to 275° C. with forces of 700 to 10,000 lbs. After cooling, samples were cut into ⅜" wide and 3"long strips.

The instrument is interfaced with a computer for controlling the test speed and other test parameters, and for collecting, calculating and reporting the data. The tensile stress-strain properties of the film are determined according to ASTM Method D882-97. These tensile properties are measured at ambient temperature (about 20-25° C.). The procedure is as follows:

(1) choose appropriate jaws and load cell for the test; the jaws should be wide enough to fit the sample, typically 1"wide jaws are used; the load cells is chosen so that the tensile response from the sample tested will be between 25% and 75% of the capacity of the load cells or the load range used, typically a 500 N load cell is used;
(2) calibrate the instrument according to the manufacture's instructions;
(3) set the gauge length at 1";
(4) place the sample in the flat surface of the jaws according to the manufacture's instructions;
(5) set the cross head speed at a constant speed of 1"/min;
(6) start the test and collect data simultaneously; and
(7) calculate and report tensile properties including modulus, elongation and load at break. The average result of three samples is reported.

As used herein, the term "percent elongation" refers to the ratio obtained from dividing the length of the sample material measured at a specific condition (e.g., while the sample material is elongated under an applied force) by the length of the sample material in its undeformed state, then multiplied by 100. Thus, a sample material in its undeformed or unstrained state has a 100% elongation.

As used herein, the term "percent strain" refers to the difference between the length of the sample material measured at a certain elongation and the length of the samples material in its undeformed state, divided by the length of the sample material in its undeformed state, then multiplied by 100. Thus, a sample material in its undeformed or unstrained state has a 0% strain.

As used herein, the term "stress relaxation" or "force relaxation" refers to the percentage loss of load (i.e., tension force) between the maximum load encountered after elongating a sample material at a specific rate of strain to a predetermined length and the remaining load measured after the sample material has been held at that length for a specified period of time. Stress relaxation is expressed as percentage loss of the initial load after a specific period of time at a specific strain of a sample material.

C. Molecular Weight Determination

Number-average molecular weights are estimated by analysis of the NMR spectra of the compounds. Methyl end groups are quantified via their peak at 1 ppm while the aromatic content is quantified by their peak at approximately 7-8 ppm. Methylene esters are quantified via their peak at approximately 4-4.5 ppm and aliphatic methylenes are quantified via their peaks from 1.5-2.5 ppm. One of skill in the art would recognize spectra of other groups in light of the present disclosure. From these quantified values a product structure is determined and the molecular weight is calculated.

D. Shear Viscosity Test

Shear viscosity of the blend can be measured using the ARES Polymer Melt Rheometer (manufactured by Rheometrics) in the parallel plate mode. The sample handling and instrument operation generally follow the operating manual provided by the manufacturer, except for the specific testing conditions described herein. In this test, the sample is placed between two parallel plates that are 25 mm in diameter and have 1 mm gap between them. Samples are prepared by placing 5 g of material between 2 PTFE (Teflon) sheets and placed in a Carver Press at 175° C. The sample is allowed to heat up and 700 lbs of pressure is applied to the material. Metal shims with a thickness of 1.2 mm are used to control thickness. Once pressed, the sample is removed from the press and immediately placed between 2 aluminum blocks (1"thick) to rapidly cool the sample. This process of heating removes thermal history of the sample.

Depending on the material, the shear viscosity is either measured in steady or dynamic mode with the rheometer. In steady mode, the instrument performs a rate sweep, wherein the shear rate is ramped up from $0.1\ s^{-1}$ to $100\ s^{-1}$ and viscosity ($\eta$) measurements are taken at regular intervals (typically 5 points per decade of shear rate).

In dynamic mode, the complex shear viscosity $\eta^*$ is measured at $1\ s^{-1}$ oscillating at 5% strain. The instrument is operated in a temperature scan mode, wherein the temperature is ramped up at 5° C./min over the range from 100° C. to at least 50° C. above the highest phase transition temperature.

E. Force or Stress Relaxation Test

The property determined by this method may correlate with the forces a wearer experiences from an elastic component incorporated into a product. The first cycle is a prestraining step that simulates the conditions the elastic component experiences as the product is initially stretched in order to put the product on a wearer or to adjust the product to fit the wearer. The second cycle measures the reduction in elastic forces (i.e., stress relaxation) resulting from the prestraining step.

The instrument, the sample preparation and the laboratory conditions are the same as Test Method A above. The procedure is as follows:

(1) choose appropriate jaws and load cell for the test; the jaws should be wide enough to fit the sample, typically 1"(25.4 mm) wide jaws are used; the load cells is chosen so that the response from the sample tested will be between 25% and 75% of the capacity of the load cells or the load range used, typically a 50 lb (22.7 kg) load cell is used;

(2) calibrate the instrument according to the manufacturer's instructions;

(3) set the gauge length at 1"(25.4 mm) and place the sample in the instrument according to the manufacturer's instructions;

(4) set the cross head speed at a constant speed of 10"/min (0.254 m/min);

(5) Prestrain the sample to 500% strain and immediately (i.e., without holding time) return to 0% strain;

(6) Reclamp the prestrained sample to remove any slack and maintain a 1"(2.54 cm) gauge length;

(7) Start the sustained load stress relaxation test and collect data simultaneously, the sustained load stress relaxation test has the following steps:

a) go to 200% strain at a rate of 10"/min (0.254 m/min);

b) hold position for 30 seconds;

c) go to 0% strain at the at a of 10"/min (0.254 n/min); and d) calculate the stress relaxation at 200% strain as the % loss between the initial load and the load at time t of step 7(*b*) as follows:

$$\% \text{ Force Relaxation at time, } t = \frac{[(\text{initial load}) - (\text{load at time, } t)]}{(\text{initial load})} \times 100$$

The average result of three samples is reported. The load at 200% strain of step 7(*a*) is normalized to 85 gsm as follows: the load at 200% strain from the plot is divided by the width of the sample, then multiplied by a normalizing factor, which is 85/(½(actual weight of the sample/(width*gauge length)) of sample in $m^2$)), or 85/(½*(actual weight of the sample)/ $(6.47 \times 10^{-4})$) if the sample dimension is measured in inches.

EXAMPLES

Example 1

A phase change solvent having the general formula (I) is prepared by combining 260 grams (2 moles) of octanol with 404 grams (2 moles) of terephthaloyl chloride and 202 grams (1 mole) of 1,12-dodecanediol in 1500 ml of chloroform in a reaction flask. The mixture is allowed to react at 55° C. for 20 hours with constant stirring and under a vacuum, which removes HCl generated by the reaction. The reaction is terminated by cooling the mixture to room temperature. The resulting reaction mixture is poured into a large quantity of methanol to precipitate the product. The precipitant is collected over a filter, washed with 500 ml of methanol 3 times and dried at 45° C. in an vacuum oven for 20 hours. The resulting product has a number-average molecular weight of about 720 and an AA ratio of 2.3. FIG. 1 a DSC thermogram illustrating the phase changes of the phase change solvent of Example 1. As shown in FIG. 1, the phase change solvent exhibits multiple first order transitions (shown here as endothermic peaks) in the range from about 60° C. to about 100° C., indicating that this phase change solvent readily crystallizes at or below about 100° C.

Example 2

A phase change solvent having the general formula (I) is prepared by combining 260 grams (2 moles) of octanol with 502 grams (2 moles) of naphthalene-dicarboxylic acid chloride and 146 grams (1 mole) of 1,8-octanediol in 1500 ml of chloroform in a reaction flask. The reaction conditions and the product collection steps are the same as in Example 1. The resulting product has a number-average molecular weight of about 770 and an AA ratio of 1.2.

Example 3

Figure 2:
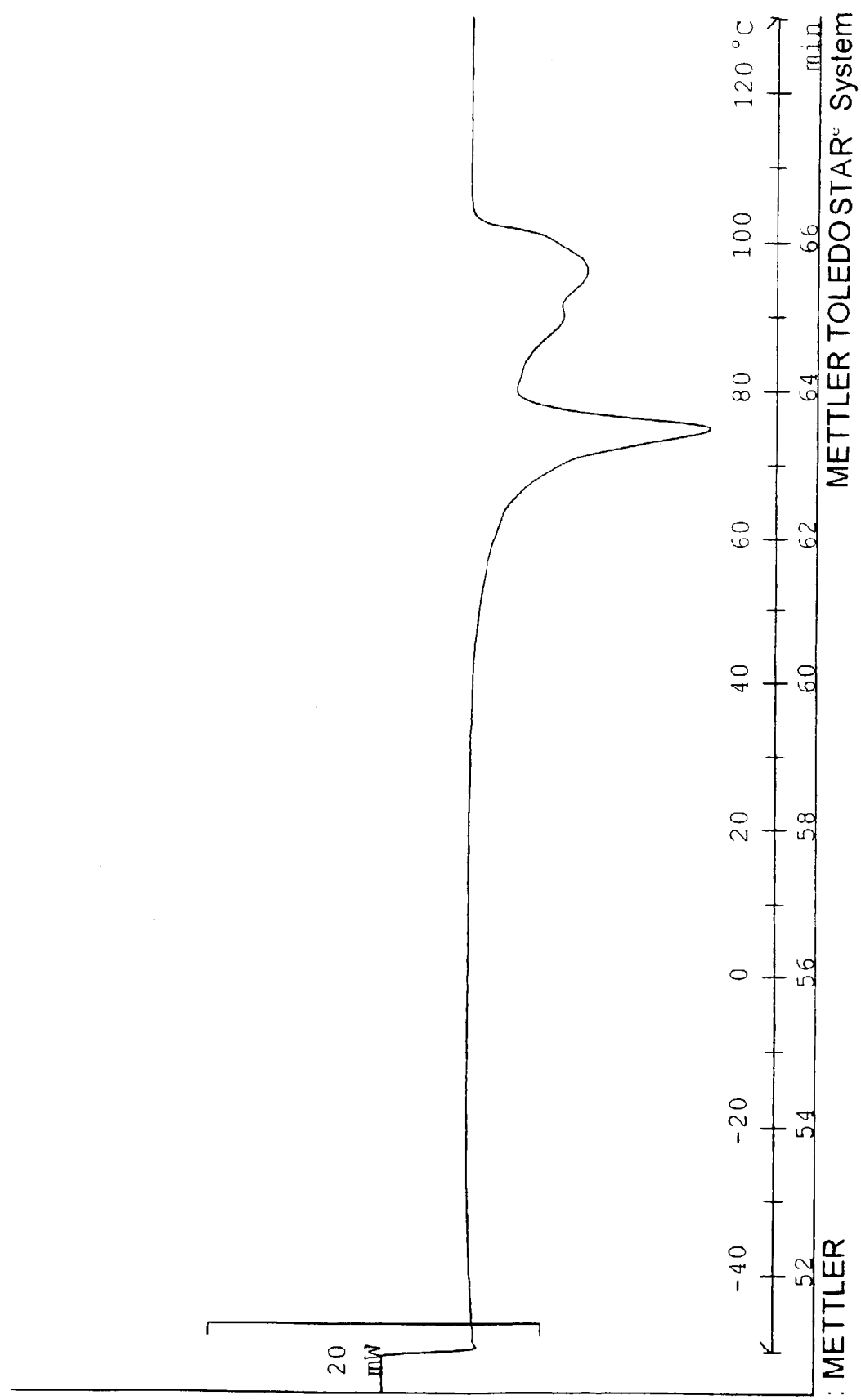
FIG. 2 is a DSC thermogram showing phase change properties of the phase change solvent of Example 3. The y axis or ordinate represents increasing exothermic heat flow.

A phase change solvent having the general formula (II) is prepared by combining 130 grams (1 moles) of octanol with 404 grams (2 moles) of terephthaloyl chloride and 404 grams (2 mole) of 1,12-dodecanediol in 1200 ml of chloroform in a reaction flask. The reaction conditions and the product collection steps are the same as in Example 1. The resulting product has a number-average molecular weight of about 790 and an AA ratio of 2.7. FIG. 2 is a DSC thermogram showing the phase change properties of the solvent of this example.

Example 4

A phase change solvent having the general formula (II) is prepared by combining 130 grams (1 moles) of octanol with 404 grams (2 moles) of terephthaloyl chloride in 250 ml of chloroform in a reaction flask. The mixture is allowed to react at 55° C. for 20 hours with constant stirring and under a vacuum, which removes HCl generated by the reaction. The reaction is terminated by cooling the mixture to room temperature. The resulting product is concentrated via vacuum distillation at the boiling point of chloroform followed by dilution with 250 ml of acetone and 2 ml of water. After stirring for 4 hours, the solution is filtered and concentrated by vacuum distillation at the boiling point of acetone and the product is dried at 45° C. under vacuum for 20 hours. The resulting product has a number-average molecular weight of about 280 and an AA of 1.3.

Example 5

A phase change solvent having the general formula (I) is prepared by combining 260 grams (2 moles) of octanol with 502 grams (2 moles) of naphthalene-dicarboxylic acid chloride and 202 grams (1 mole) of 1,12-dodecanediol in 1500 ml of chloroform in a reaction flask. The reaction conditions and the product collection steps are the same as in Example 1. The resulting product has a number-average molecular weight of about 820 and an AA ratio of 1.4.

Example 6

A phase change solvent having the general formula (II) is prepared by combining 161 grams (1 moles) of octanol with 404 grams (2 mole) of 1,12-dodecanediol in 1000 ml tetrahydrofuran and 195 grams (5 moles) of potassium in a reaction flask. After stirring for 24 hours, 346 grams (2 moles) of 1,4-dichloroxylene is added to the mixture. The mixture is allowed to react at 55° C. for 20 hours with constant stirring. The reaction is terminated by cooling the mixture to room temperature. The resulting mixture is poured into a large quantity of methanol to precipitate the product. The precipitant is collected over a filter, washed with 500 ml of methanol 3 times, and dried at 45° C. under vacuum for 20 hours. The resulting product has a number-average molecular weight of about 720 and an AA ratio of 2.7.

Example 7

Figure 3:
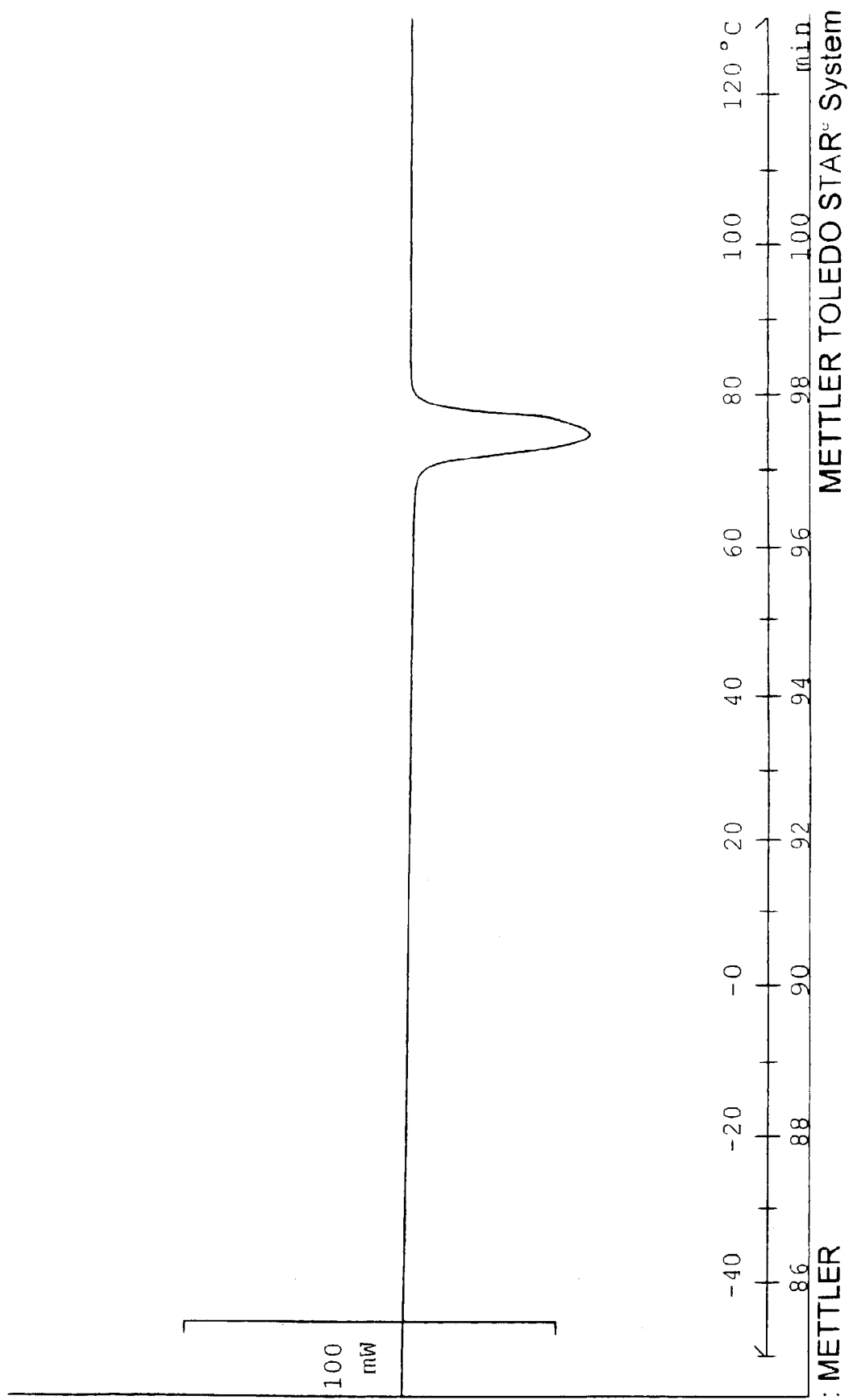
FIG. 3 is a DSC thermogram showing phase change properties of the phase change solvent of Example 7. The y axis or ordinate represents increasing exothermic heat flow.

A phase change solvent having the general formula (III) is prepared by combining 162.5 grams (1 moles) of octanoyl chloride with 220 grams (2 moles) of hydroquinone in 400 ml of chloroform in a reaction flask. The mixture is allowed to react at 55° C. for 20 hours with constant stirring and under a vacuum, which removes HCl generated by the reaction. The reaction is terminated by cooling to room temperature. The resulting product is concentrated via vacuum distillation at the boiling point of chloroform followed by dilution with 250 ml of acetone and 2 ml of water. After stirring for 4 hours, the mixture is filtered and concentrated by vacuum distillation at the boiling point of acetone and the product is dried at 45° C. under vacuum for 20 hours. The precipitant is collected over a filter, washed with 500 ml of methanol 3 times and dried at 45° C. under vacuum for 20 hours. The resulting product has a number-average molecular weight of about 240 and an AA of 1.3. FIG. 3 is a DSC thermogram showing the phase change properties of the solvent of this example.

Example 8

A phase change solvent having the general formula (I) is prepared by combining 260 grams (2 moles) of octanol with 202 grams (1 moles) of terephthaloyl chloride in 400 ml of chloroform in a reaction flask. The mixture is allowed to react at 55° C. for 20 hours with constant stirring and under a vacuum, which removes HCl generated by the reaction. The reaction is terminated by cooling the mixture to room temperature. The resulting product is collected by pouring the mixture into a large quantity of cold methanol (0° C.) to precipitate the product. The precipitant is collected over a filter, washed with 500 ml of cold methanol (at 0° C.) 3 times and dried at 25° C. under vacuum for 20 hours. The resulting product has a number-average molecular weight of about 390 and an AA ratio of 2.7.

Alternatively, the phase change solvents are prepared by using 2 moles of C10-C16 alcohols instead of octanol.

Examples 9-20

An elastomeric composition is prepared by mixing and stirring the phase change solvent of Example 1 and SEPTON® S4033 (available from Kuraray America, Inc., New York, N.Y.) at 120° C. for 4 hours or until the sample appears to be homogeneous. The mixture is cooled to room temperature. Mineral oil, DRAKEOL® Supreme (available from Pennzoil Co., Penrenco Div., Karns City, Pa.) is then added to the mixture and stirred at room temperature for 16 hours to form an elastomeric composition.

Alternatively, the composition is prepared by mixing all the components in chloroform (5 grams total weight of the composition in 45 grams of chloroform) and stirring for 2 hours or until the mixture appears homogeneous. The mixture is then poured into a TEFLON® dish and let dry at room temperature overnight. The mixture and the TEFLON® dish are placed in a vacuum oven for an hour at 60° C.

The above blending method is merely exemplary. Other conventional blending methods using batch mixers, screw extruders, and the like, may also be used.

Comparative Examples 1-2

Elastomeric compositions (comparative examples 1-2) are prepared with SEPTON® S4033 (from Kuraray America, Inc. New York, N.Y.), polystyrene NOVACOR® PS 3900 (from Nova Chemicals, Inc., Monaca, Pa.), and mineral oil, DRAKEOL® Supreme (from Pennzoil Co., Penrenco Div., Karns City, Pa.). Elastomeric compositions are also prepared with VECTOR® 4211 (available from Dexco Chemical Company, Houston, Tex.), instead of SEPTON®. The compositions may be prepared by any of the methods described above. The components (shown in weight percent) for the comparative examples and their properties, in comparison with exemplary compositions of the present invention are listed in TABLEs 1 and 2.

TABLE 1

| Example | Comp. 1 | Comp. 2 | 9 | 10 | 11 | 12 | 13 | 14 | 15 |
|---|---|---|---|---|---|---|---|---|---|
| SEPTON® S-4033 | 50 | 40 | 50 | 50 | 50 | 40 | 40 | 50 | 40 |
| Polystyrene | 20 | 30 | | | | | | | |
| Mineral oil | 30 | 30 | 30 | 25 | 20 | 40 | 30 | 20 | 30 |
| Example 1 (C8-C12)* | | | 20 | 25 | 30 | 20 | 30 | | |
| Example 2 (C8-C8)** | | | | | | | | 30 | 30 |
| η @ 175° C., 1 s$^{-1}$ steady (Pa-s) | 5770 | 3209 | 429 | 237 | 89 | 51 | 24 | 32 | 37 |
| Norm^Peak Load (N/m) | 501 | 460 | 612 | 642 | 513 | 360 | 308 | 341 | 133 |
| Peak Strain (%) | 506 | 870 | 705 | 621 | 550 | 680 | 580 | 490 | 486 |
| Norm^Load @ 200% strain (N/m) | 118 | 154 | 88 | 96 | 126 | 63 | 78 | 123 | 78 |
| % Force Relaxation @ 200% strain, RT, 30 sec | 12 | 17 | 10 | 11 | 15 | 10 | 12 | 14 | 12 |

*(C8-C12) represents a phase change solvent of formula (I) having R, R' = H, y = 8, x = 12 and n = 2.
**(C8-C8) represents a phase change solvent of formula (I) having R, R' = H, y = 8, x = 8 and n = 2.
^Normalized to 85 gsm The above examples show that, with respect to Comparative Examples 1-2, the incorporation of a phase change solvent significant decreases shear viscosity and provides satisfactory elastic and tensile properties. Examples 9-15 further show that the phase change solvent is more effective than mineral oil in lowering the shear viscosity of the elastomeric composition without substantially compromising elastic and tensile properties. In some of the above examples, mechanical properties were improved over the control.

TABLE 2

| Example | Comp. 3 | Comp. 4 | 16 | 17 | 18 | 19 | 20 |
|---|---|---|---|---|---|---|---|
| VECTOR® 4211 | 50 | 70 | 50 | 50 | 50 | 70 | 70 |
| Polystyrene | 20 | 10 | | 10 | 10 | | |
| Mineral oil | 30 | 20 | 30 | 20 | 20 | 20 | 20 |
| Example 1 (C8-C12)* | | | 20 | 20 | | 10 | |
| Example 2 (C8—C8)** | | | | | 20 | | 10 |
| η* @ 175° C., 1 s$^{-1}$ dynamic (Pa-s) | 4945 | 3911 | 11 | 70 | 163 | 1061 | 1440 |
| Norm^Peak Load (N/m) | 61 | 377 | 54 | 391 | 232 | 271 | 302 |
| Peak Strain (%) | 322 | 834 | 348 | 856 | 653 | 1027 | 1210 |
| Norm.^Load @ 200% strain (N/m) | 31 | 79 | 38 | 53 | 59 | 71 | 60 |
| % Force Relaxation @ 200% strain, RT, 30 sec | 8 | 11 | 10 | 12 | 11 | 9 | 9 |

*(C8-C12) represents a phase change solvent of formula (I) having R, R' = H, y = 8, x = 12 and n = 2.
**(C8—C8) represents a phase change solvent of formula (I) having R, R' = H, y = 8, x = 8 and n = 2.
Normalized to 85 gsm The above examples show even for compositions which comprise a relatively melt flowable and more processable styrenic TPE (such as VECTOR®), the incorporation of a phase change solvent is still effective in lowering the shear viscosity without substantially compromising the tensile and elastic properties.

Example 21

A phase change solvent having the general structure (V) is prepared by a polymerization that opens a lactone ring. Caprolactone is polymerized via addition of 0.1 moles of di-isopropyl aluminum chloride to a reactor containing 100 grams of caprolactone which is heated at 80° C. for 24 hours. The reaction product is isolated by precipitation from hexanes. The molecular weight is determined by the ratio of grams monomer/moles initiator; theoretical mw=100 grams/ 0.1 mole=1000 g/mol.

Example 22

A phase change solvent having the general structure (V) is prepared by combining phosgene, a diol, and an alcohol as follows. Phosgene (2 moles) as a benzene solution is combined with 202 grams (1 mole) of 1,12-dodecanediol and 260 grams (2 moles) of octanol. This is heated at 40° C. for 24 hours. The reaction product is isolated by precipitation from methanol.

Example 23

A phase change solvent having the general structure (X) is prepared by combining a diamine and a diacid chloride and an acid chloride as follows. 1,6-Hexanediamine (348 grams (3 moles)) is combined with 348 grams (2 moles) of 1,6-hexanedicarboxylic acid chloride and 239 grams (1 mole) of 1-decanoic acid chloride in a mixture of 1000 grams of benzene and 1000 grams of pyridine. This is heated at 60° C. for 24 hours. The reaction product is isolated by precipitation from hexanes.

Example 24

A phase change solvent having the general structure (VIII) is prepared by combining di-isocyanate, a diol, and an alcohol as follows. Toluene di-isocyanate (348 grams (2 moles)) is combined with 202 grams (1 mole) of 1,12-dodecanediol and 260 grams (2 moles) of octanol. The reaction is carried out at 60° C. for 24 hours. The reaction product is isolated by precipitation from methanol.

Example 25

A blended composition comprising polyethylene terephthalate with 20% phase change solvent of Example 1, i.e., structure (I) having y=8, x=12, and n=2, (aka C8-C12 solvent) is produced as follows. Cleartuf 8406 (4.0 g) (Shell Chemical Co.) is combined with 1.0 g C8-C12 oligomeric terephthalate solvent and melt pressed at 275° C. and 10,000 lbs of force for 5 sec. This process is repeated until a uniform film (approx 0.040" thickness) results and is visually homogeneous.

Example 26

A blended composition comprising polyamide with 20% phase change solvent of Example 1 (C8-C12 solvent) is produced as follows. Nylon 6 (4.0 g) (Aldrich Chem Co.) is combined with 1.0 g C8-C12 oligomeric terephthalate solvent and melt pressed at 275° C. and 10,000 lbs of force for 5 sec. This process is repeated until a uniform film (approx 0.040" thickness) results and is visually homogeneous.

Example 27

A blended composition comprising atactic polypropylene with 16% phase change solvent of Example 1 (C8-C12 solvent) is produced as follows. Atactic PP (4.2 g) (P&G labs) is combined with 0.8 g C8-C12 oligomeric terephthalate solvent and melt pressed at 275° C. and 5,000 lbs of force for 5 sec. This process is repeated until a uniform film (approx 0.040" thickness) results and is visually homogeneous.

Example 28

A blended composition comprising atactic polypropylene with 16% C18 dialkyl terephthalate solvent is produced as follows. Atactic PP (4.2 g) (P&G labs) is combined with 0.8 g C18 dialkyl terephthalate additive and melt pressed at 275° C. and 5,000 lbs of force for 5 sec. This process is repeated until a uniform film (approx 0.040" thickness) results and is visually homogeneous.

Example 29

A blended composition comprising 4.0 g of atactic polypropylene mixed with 1.0 g terephthalate solvent is produced. It is then possible to process the mixture without special equipment or conditions that are required for the neat material. The mixture can be formed, extruded, or molded at a temperature of 230° C. rather than 280° C. that was required for the neat material.

Example 30

A blended composition comprising 4.2 g of atactic polypropylene (mw 2,000,000) mixed with 0.8 g terephthalate solvent is produced. The viscosity of the mixture at 275° C. is reduced by a factor of 84 relative to the neat material. This reduction in viscosity provides the ability to process this formulation at the same viscosity as a 500,000 molecular weight polypropylene. The mechanical properties of the 2,000,000 mw polypropylene are substantially better than the 500,000 mw PP. The stress relaxation of the 2,000,000 mw PP is 24% while the 500,000 mw PP has a stress relaxation of 40%.

TABLE 3 provides shear viscosity of the neat thermoplastic polymer as compared to the viscosity of the blended compositions of Examples 27, 28, 25, and 26, respectively.

TABLE 3

Shear Viscosity of Neat Polymer vs. Blended Composition

| Polymer | Viscosity of neat polymer Pa-s @T | Viscosity with solvent Pa-s @T |
|---|---|---|
| atactic PP | 84,000 @ 230° C. | 1030 @230° C. C8-C12 oligomer |
| atactic PP | 84,000 @ 230° C. | 8090 @230° C. C18 dialkyl terephthalate |
| PET (Shell Cleartuf 8406) | 140 @280° C. | 10 @280° C. C8-C12 oligomer |
| Nylon 6 (Aldrich) | 145 @250° C. | 49 @250° C. C8-C12 oligomer |

The data of Table 3 demonstrate that shear viscosity is lowered by a factor of about 80, 10, 14, and 3, respectively, by the blending of a phase change solvent with the cited polymers.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. A composition comprising: a phase change solvent having the general formula:

$$R'\text{-}P_y\text{-}(Q\text{-}P_x)_{n-1}\text{-}Q\text{-}P_y\text{-}R;\qquad\qquad\text{(I)}$$

$$R'\text{-}P_y\text{-}(Q\text{-}P_x)_n\text{-}R;\text{ or}\qquad\qquad\text{(II)}$$

$$R'\text{-}(Q\text{-}P_x)_{n-1}\text{-}Q\text{-}P_y\text{-}R\qquad\qquad\text{(IV-a)}$$

wherein

Q is an unsubstituted difunctional aromatic moiety;

P is $CH_2$;

R and R' are independently selected from the group consisting of H and $CH_3$;

x and y are independently an integer from 1 to 30, and x≠y;

n is an integer from 3 to 7 when the solvent has the formula (II); and n is an integer from 3 to 8 when the solvent has the formula (I) or (IV), wherein the phase change solvent has a phase change in a temperature range from 40° C. to 250° C.

2. The composition of claim 1 wherein the phase change solvent has a number-average molecular weight from about 150 to about 5,000.

3. The composition of claim 1, wherein an AA ratio ($C_{aliphatic}$ to $C_{aromatic}$) of the phase change solvent ranges from about 0.25 to about 4.

* * * * *

UNITED STATES PATENT AND TRADEMARK OFFICE
CERTIFICATE OF CORRECTION

PATENT NO. : 7,524,984 B2
APPLICATION NO. : 10/429531
DATED : April 28, 2009
INVENTOR(S) : Smith et al.

Page 1 of 1

It is certified that error appears in the above-identified patent and that said Letters Patent is hereby corrected as shown below:

<u>Title Page, Other Publications</u>

Line 3, delete "(1995)" and insert --(1996)--.

<u>Cover Page, Other Publications, Page 2</u>

Line 2, delete "sinle" and insert --single--.

<u>Column 2</u>

Line 14, delete "theological" and insert --rheological--.

<u>Column 14</u>

Line 61, delete the second "(VII)" and insert --(VIII)--.

<u>Column 18</u>

Line 17, after the number 0.254 delete "n" and insert --m--.

<u>Column 19</u>

Line 17, delete "(II)" and insert --(III)--.

<u>Column 21</u>

Line 66, insert --^-- in front of the word Normalized.

Signed and Sealed this

Seventeenth Day of November, 2009

David J. Kappos
*Director of the United States Patent and Trademark Office*